United States Patent [19]

Pechhold

[11] 4,355,119

[45] Oct. 19, 1982

[54] OLIGOMERIC FORMAL DIOLS OF POLY(TETRAMETHYLENE ETHER) GLYCOL AND POLYURETHANES PREPARED THEREFROM

[75] Inventor: Engelbert Pechhold, Chadds Ford, Pa.

[73] Assignee: E. I. DuPont de Nemours and Company, Wilmington, Del.

[21] Appl. No.: 318,946

[22] Filed: Nov. 6, 1981

Related U.S. Application Data

[62] Division of Ser. No. 180,878, Aug. 25, 1980, Pat. No. 4,340,719.

[51] Int. Cl.$^3$ ............................................. C08G 18/14
[52] U.S. Cl. ..................................... 521/159; 521/163; 521/164; 528/60; 528/61; 528/62; 528/63; 528/64; 528/65; 528/73; 528/76
[58] Field of Search ............... 521/159, 163, 164, 176; 528/61, 60, 62, 63, 64, 65, 73, 76

[56] References Cited

U.S. PATENT DOCUMENTS 2,929,800  3/1960  Hill ............................. 260/32.6 NR
2,961,428  11/1960  Muller et al. ........................ 260/49
3,959,227  5/1976  Chang et al. .......................... 260/67

FOREIGN PATENT DOCUMENTS 850178  9/1960  United Kingdom .

OTHER PUBLICATIONS

Schonfeld, Journal of Polymer Science, vol. 59, pp. 87-92 (1962).

Primary Examiner—Maurice J. Welsh

[57] ABSTRACT

Oligomeric formal diols are prepared by coupling segments of PTMEG, each having a molecular weight of 1000-3000, with formaldehyde. The formal diols are useful in preparing polyurethanes.

4 Claims, No Drawings

OLIGOMERIC FORMAL DIOLS OF POLY(TETRAMETHYLENE ETHER) GLYCOL AND POLYURETHANES PREPARED THEREFROM

CROSS REFERENCE TO RELATED APPLICATION

This application is a divisional of application Ser. No. 180,878, filed Aug. 25, 1980 now U.S. Pat. No. 4,340,719.

TECHNICAL FIELD

This invention relates to oligomeric formal diols of poly(tetramethylene ether) glycol (PTMEG). It is more particularly directed to such formal diols made by coupling up to four PTMEG segments with formaldehyde.

The invention also related to polyurethanes made with these oligomeric formal diols.

BACKGROUND AND SUMMARY OF THE INVENTION

Polyurethanes have been known and used for many years, and the basic general chemistry for their preparation, the reaction of a polyol, a polyisocyanate and a chain extender, is well documented.

A polyol frequently used for this purpose is PTMEG. In some applications, especially where a polyurethane of high modulus and hardness is needed, it is desirable to use a PTMEG with a molecular weight of over about 2000. Unfortunately, a PTMEG of such high molecular weight is difficult to make and use because its high viscosity hinders handling and subsequent reaction.

It has now been found that this difficulty can be eliminated by coupling, with formaldehyde, two, three or four segments of PTMEG, each having a number average molecular weight of 1000–3000. This gives an oligomeric formal diol with a number average molecular weight of 2000–12,000, and with a viscosity much lower than that of a PTMEG of equivalent molecular weight. Moreover, when such a formal diol is used to prepare a polyurethane, the product shows no significant degradation of properties compared to one made with an equivalent PTMEG.

DETAILED DESCRIPTION OF THE INVENTION

The oligomeric formal diols of the invention are made by catalytically reacting a suitable PTMEG with formaldehyde.

The PTMEG starting material must have a number average molecular weight of 1000–3000, preferably 2000–3000. Number average molecular weight is determined by first determining the hydroxyl number of the sample by titrating it with acetic anhydride according to ASTM-D-1638 and then converting this number to number average molecular weight according to the formula $$\text{Molecular weight} = \frac{56,000 \times n}{\text{hydroxyl number}}$$

where n is the hydroxyl functionality of the sample.

The PTMEG can be any of those commercially available, or can be prepared by any of the well-known methods of catalytically polymerizing tetrahydrofuran.

The formaldehyde can be used as a gas, as an aqueous solution, or in the form of paraformaldehyde. As used herein, "formaldehyde" means any of these forms. If an aqueous solution is used, the water thus introduced must later be removed from the reaction mass, and the use of paraformaldehyde is therefore preferred.

The amounts of PTMEG and formaldehyde used are of course governed by the molecular weight desired in the product, and will be 2, 3 or 4 moles of PTMEG for 1, 2 or 3 moles of formaldehyde, respectively. It is preferred to use an excess over the 1–3 moles specified when paraformaldehyde is used because it has a tendency to sublime under reaction conditions; it is desirable that this loss be compensated for.

The reaction can be carried out in an aromatic hydrocarbon like toluene or xylene, or it can be carried out in bulk, using the PTMEG itself as the reaction medium.

The catalyst can be any strongly acidic cationic ion-exchange resin bearing —$SO_3H$ groups, insoluble in the PTMEG. "Insoluble" means that the amount of resin which dissolves in the PTMEG under process conditions will give the formal diol product an acid number of no greater than 0.05 mg of KOH per gram.

For purposes of the invention, the nature of the "backbone" of the resin is unimportant. The most common of the commercially available resins of this type have backbones which are of the polystyrene type, but resins having other backbones can be used. Preferred among the polystyrene type resins, and preferred for use is one sold by the Rohm & Haas Company of Philadelphia, PA, as Amberlyst® XN-1010. This macroreticular resin has a cation exchange capacity of 3.1 milliequivalents per gram, a surface area of 450 square meters per gram, a porosity of 41%, and a mean pore diameter of 50 Angstrom units.

The catalyst is used at a concentration of 1–10%, by weight of the PTMEG, preferably 5–10%.

The reaction is carried out at a temperature of 60°–110° C., preferably 70°–90° C. If the reaction is conducted in an aromatic hydrocarbon medium, the water of condensation formed can be removed by azeotropic distillation. If it is conducted in bulk, the water can be removed under vacuum or by sweeping the reaction zone with nitrogen.

When an oligomeric diol having the desired molecular weight has been obtained, as determined by periodic sampling and analysis, the reaction mass is cooled to ambient temperature and the catalyst and unreacted paraformaldehyde (if it is used) are removed by filtration. If formaldehyde is used, any which remains unreacted can be removed under vacuum.

The resulting oligomeric formal diol will have a number average molecular weight in the range 2000–12,000, preferably 4000–9000, the actual molecular weight of course depending on the molecular weight of the PTMEG starting material and the number of segments coupled. The formal diol will have a melting point of 18°–22° C. and will have a viscosity within the range 1.0–10.0 pascal seconds, as determined with a glass capillary viscometer, according to ASTM D-445 and ASTM D-2515, at a temperature of 60° C.

A polyurethane can be prepared from such an oligomeric formal diol by reacting it with an organic polyisocyanate and an aliphatic polyol or polyamine chain extender, as is well known in the art.

The polyisocyanates used in preparing the polyurethanes can be any of the aliphatic or aromatic polyisocyanates ordinarily used to prepare polyurethanes. Illustrative are 2,4-toluene diisocyanate
2,6-toluene diisocyanate
hexamethylene-1,6-diisocyanate
tetramethylene-1,4-diisocyanate
cyclohexane-1,4-diisocyanate
naphthalene-1,5-diisocyanate
diphenylmethane-4,4'-diisocyanate
xylylene diisocyanate
hexahydro xylylene diisocyanate
dicyclohexylmethane-4,4'-diisocyanate
1,4-benzene diisocyanate
3,3'-dimethyoxy-4,4'-diphenyl diisocyanate
m-phenylene diisocyanate
isophorone diisocyanate
polymethylene polyphenyl isocyanate
4,4'-biphenylene diisocyanate
4-isocyanatocyclohexyl-4'-isocyanatophenyl methane
p-isocyanatomethyl phenyl isocyanate.
Mixtures of isocyanates can also be used.

The isocyanates preferred for use because of the desirable properties they confer on the polyurethane products are diphenylmethane-4,4'-diisocyanate and the toluene diisocyanates.

The chain extenders used in preparing the polyurethanes can be any of the aliphatic polyols, or any of the aliphatic or aromatic polyamines ordinarily used to prepare polyurethanes.

Illustrative of the aliphatic polyols which can be used as chain extenders are
1,4-butanediol
ethylene glycol
1,6-hexanediol
glycerine
trimethylolpropane
pentaerythritol
1,4-cyclohexane dimethanol
phenyl diethanolamine
Diols like hydroquinone bis(betahydroxyethyl)ether, tetrachlorohydroquinone-1,4-bis(betahydroxyethyl)ether and tetrachlorohydroquinone-1,4-bis(betahydroxyethyl)sulfide, even though they contain aromatic rings, are considered to be aliphatic polyols for purposes of the invention.

Aliphatic diols of 2-10 carbon atoms are preferred. Especially preferred is 1,4-butanediol. Mixtures of diols can also be used.

Illustrative of the polyamines which can be used as chain extenders are
p,p'-methylene dianiline and complexes thereof with alkali metal chlorides, bromides, iodides, nitrites and nitrates.
4,4'-methylene bis(2-chloroaniline)
dichlorobenzidine
piperazine
2-methylpiperazine
oxydianiline
hydrazine
ethylenediamine
hexamethylenediamine
xylylenediamine
bis(p-aminocyclohexyl)methane
dimethyl ester of 4,4'-methylenedianthranilic acid
p-phenylenediamine
m-phenylenediamine
4,4'-methylene bis(2-methoxyaniline)
4,4'-methylene bis(N-methylaniline)
2,4-toluenediamine
2,6-toluenediamine
benzidine
3,4'-dimethylbenzidine
3,3'-dimethoxybenzidine
dianisidine
1,3-propanediol bis(p-aminobenzoate)
isophorone diamine
1,2-bis(2'-aminophenylthio)ethane.

The amines preferred for use are 4,4'-methylene bis(2-chloroaniline), 1,3-propanediol bis(p-aminobenzoate) and p,p'-methylenedianiline and complexes thereof with alkali metal chlorides, bromides, iodides, nitrites and nitrates. Mixtures of amines can also be used.

The polyurethanes can be prepared in two steps, the first of which is conducted under nitrogen at ambient pressure to prevent oxidation of the reactants and product, and to prevent exposure of the reaction mass to atmospheric moisture. In the first step, the oligomeric formal diol starting material is dried by heating it at a temperature of 80°-100° C. under vacuum, and is then held at 60°-125° C., preferably about 70°-90° C., while a stoichiometric excess, preferably twofold to tenfold, of organic diisocyanate is added, with stirring. The actual amount of isocyanate used depends on the molecular weight of the oligomeric formal diol, as is well known in the art. The reaction mass is held for about 1-4 hours at 60°-125° C., with stirring, and the free isocyanate content of the mass is then determined by titrating it with di-n-butylamine, as described in Analytic Chemistry of the Polyurethanes, Volume XVI, Part III, D. J. David and H. B. Staley, Wiley-Interscience, 1969, pages 357-359.

In the second step, an amount of polyamine or polyol chain extender calculated to give an isocyanate/hydroxyl or amine mole ratio of about 0.9-1.1 to 1 in the reaction mass, preferably 1-1.05/1, is degassed at about 30°-120° C. and 1330-5330 Pa (10-50 mm Hg) pressure and quickly added to the reaction mass.

A conventional curing catalyst can be added at this point if desired. Illustrative of catalysts which can be used are dibutyltin dilaurate and stannous octoate. The catalyst can be added to the reaction mass to give a concentration of about 0.001-0.1%, by weight, preferably about 0.01%.

The reaction mass is held with stirring at 60°-130° C. until it is homogeneous, which normally takes 1-5 minutes. The mass is then poured into molds, preferably preheated to 100°-120° C., and then cured at about 100°-120° C. at a pressure of 1700-2500 kPa for from 5 minutes to several hours. The casting is then cooled, removed from the mold, aged for about one week at ambient temperature, and is then ready for use.

The polyurethanes can also be made by reaction-injection and liquid-injection molding techniques, whereby the starting materials are simultaneously injected and mixed in a mold, preferably together with a conventional polyurethane catalyst and then subjected to pressures ranging from ambient to several million pascals and temperatures ranging from ambient to 150° C. Use of a foaming agent such as a fluorocarbon or water is optional.

The polyurethanes thus prepared are characterized by their high modulus and hardness, which suits them for use in fabricating automobile bumpers, cast tires and the like.

BEST MODE

In the following description, all parts are by weight.
A reactor was charged with

| | |
|---|---|
| PTMEG, MW$_n$ 2900 | 580 parts (0.2 mole) |
| Paraformaldehyde | 12.8 parts (0.4 mole) |
| Amberlyst ® XN-1010 | 30 parts |
| Toluene | 500 parts. |

This mixture was heated to reflux temperature and held there with stirring for three hours while the toluene-water azeotrope was continuously withdrawn. The mixture was then cooled to ambient temperature, filtered and stripped of toluene in a rotary evaporator, to give an oligomeric formal diol having a number average molecular weight of 6757 and a viscosity of 4.42 pascal seconds.

The resulting oligomeric formal diol, 130 parts, was mixed with 0.65 parts of tetrakis methylene 3-(3',5'-di-tert-butyl-4'-hydroxyphenyl propionate) methane, a stabilizer against oxidative degradation sold by Ciba-Geigy as Irganox ® 1010. This mixture was dried for one hour at 95° C. and a vacuum of 1333-5330 Pa (10-40 mm of Hg).

Heating was then stopped and 34.6 parts of liquid diphenylmethane-4,4'-diisocyanate were added to the mixture, with stirring. A nitrogen sweep of the reaction zone was begun. Stirring was continued for 5 minutes, and the mixture was then again brought to and held at 95° C., with stirring, for 2 hours, to give a product having a free isocyanate content of 5.95%, as determined by the di-n-butylamine titration technique.

155.8 Parts of the resulting prepolymer were then heated at 95° C. for 1 hour at a pressure of 1333-5330 Pa to remove entrapped air. Heating was then stopped and to the mixture were added, with stirring, 9.46 parts of 1,4-butanediol, preheated to 60° C. This mixture was stirred for 4 minutes and then poured into molds preheated to 110° C., which were then pressed in a platen press at 110° C. and a platen pressure of 2155 kPa (312 psi) for 17 hours. The resulting elastomeric material was held for one week at ambient temperature and was then ready for use.

I claim:
1. A polyurethane which is the reaction product of
   (a) an oligomeric formal diol having a number average molecular weight of 2000-12,000, made by coupling up to four poly(tetramethylene ether) glycol segments, each having a number average molecular weight of 1000-3000, with formaldehyde;
   (b) an organic polyisocyanate; and
   (c) a chain extender.
2. The polyurethane of claim 1 wherein the polyisocyanate is diphenylmethane-4,4'-diisocyanate or a toluene diisocyanate.
3. The polyurethane of claim 1 wherein the chain extender is an aliphatic polyol, an aliphatic polyamine or an aromatic polyamine.
4. The polyurethane of claim 3 wherein the chain extender is an aliphatic diol of 2-10 carbon atoms.